United States Patent [19]

Webb, Jr. et al.

[11] 4,367,041
[45] Jan. 4, 1983

[54] CHROMATOGRAPH DETECTION SYSTEM

[75] Inventors: Paul A. Webb, Jr., Lawrenceville; Alan H. Small, Atlanta; Dean M. Ball, Norcross, all of Ga.

[73] Assignee: Micromeritics Instrument Corporation, Norcross, Ga.

[21] Appl. No.: 180,867

[22] Filed: Aug. 25, 1980

[51] Int. Cl.³ .............................................. G01N 21/85
[52] U.S. Cl. .................................. 356/72; 73/61.1 C; 250/565; 356/407; 356/411
[58] Field of Search ...................... 356/36, 72, 73, 407, 356/410, 411; 250/564, 565; 73/61.1 C

[56] References Cited

U.S. PATENT DOCUMENTS 3,726,127 4/1973 Putnam et al. ......................... 73/23.1
3,847,550 11/1974 Scott et al. ......................... 73/61.1 C
3,941,487 3/1976 Ehret et al. ......................... 356/411
4,136,959 1/1979 Honkawa et al. .................... 356/407

Primary Examiner—Vincent P. McGraw
Attorney, Agent, or Firm—Jones & Askew

[57] ABSTRACT

A chromatograph detection system for differentiating pure components of a chromatogram for accurate measurement or collection of such components. The light beam passing through a single detector flow cell is split and absorbance is detected at two differing wavelengths. Undesirable overlapping components are eliminated by scaling the chromatogram at one wavelength to equal the chromatogram at the other wavelength, and then subtracting the chromatograms. Purity of component substances is determined by continuously dividing the chromatogram signals to determine the absorbance ratio and its characteristics over time.

7 Claims, 11 Drawing Figures

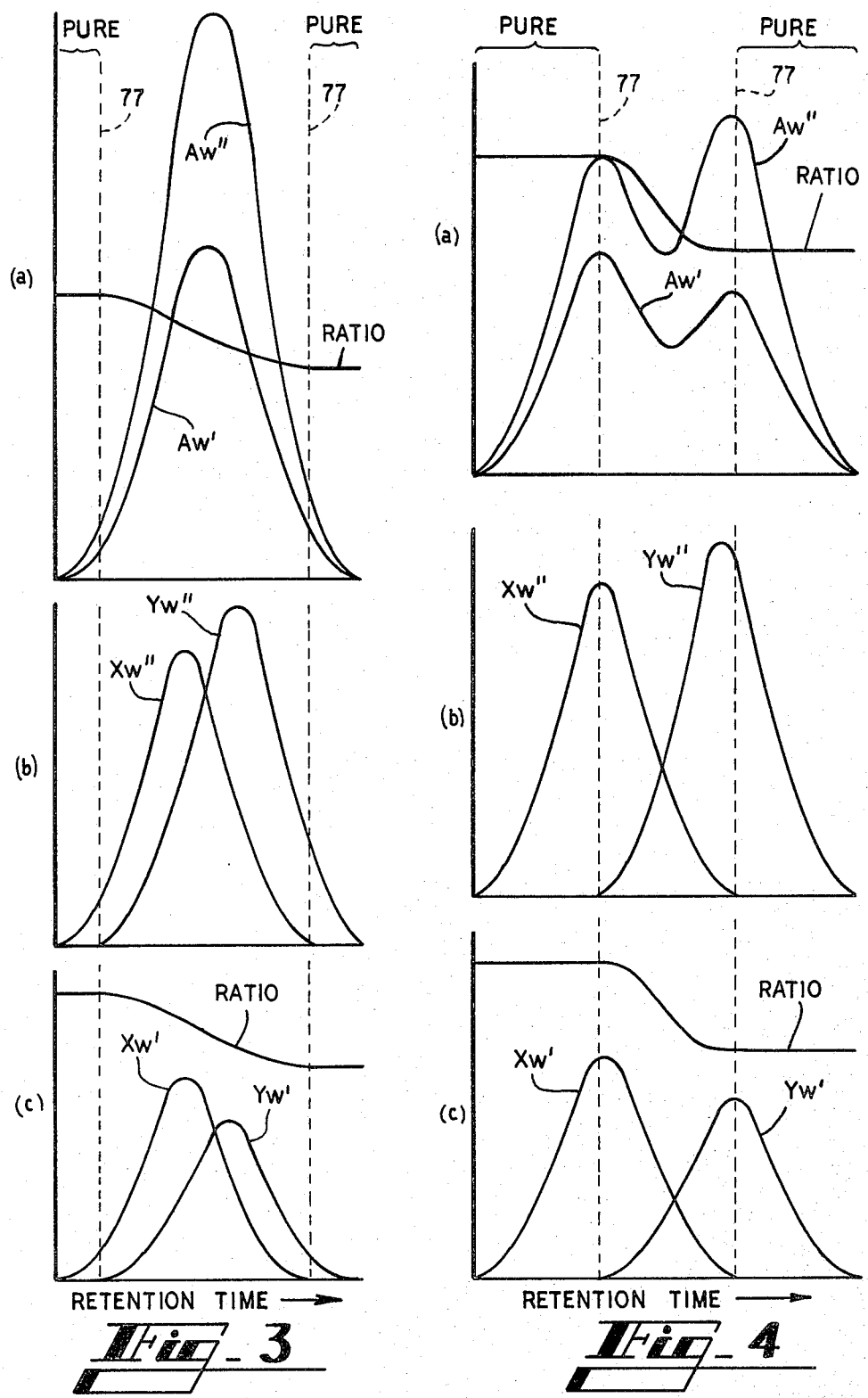

CHROMATOGRAPH DETECTION SYSTEM

TECHNICAL FIELD

The present invention relates generally to the field of liquid chromatography, and more particularly relates to a chromatograph detection system for differentiating components not completely separated by a chromatograph column to allow accurate measurement or collection of a pure substance.

BACKGROUND ART

Liquid chromatography is used to separate the components of a sample substance by passing an eluent liquid containing the sample through a column. The components of the sample in the eluent stream have different retention times within the column, and therefore exit the column in a particular sequence depending upon the nature of the components of the sample and the nature of the column. The sequence of components is detected, for example, photometrically by measuring the intensity of light passing through the eluent stream. The intensity of light is converted into an electrical signal proportional to the absorbance of the light by the component through which the light is passing, and such signal can be plotted by a chart recorder to create a chromatogram for the sample substance.

A problem experienced in liquid chromatography is that components often have very similar retention times within the chromatograph column so that the peaks of the chromatogram representing such components are overlapping or convoluted. Overlapping of peaks on the chromatogram distorts the true location and shape of the peaks and makes it difficult to accurately measure the precise retention time of the component and the amplitude of its representative peak on the chromatogram. Overlapping also makes it difficult to determine when a single pure substance is passing through the detector. Such information is needed when the purity of a substance must be confirmed, or when chromatography is used to collect quantities of highly pure components.

Most attempts in the prior art to solve the problem of distinguishing between components having identical or nearly identical retention times have been directed to increasing the separation of the components by the chromatograph column. This approach can be successful if the overlapping is not too severe. However, in many cases it is not possible to obtain sufficient separation of the peaks representing the components.

By convention, the absorbance of a substance (Aw) is defined as:

$$Aw = a \times b \times c$$

where a is the absorbance constant of the substance at the wavelength w being examined, b is the length of the flow cell through which the eluent and the detected light are being passed, and c is the concentration of the absorbing substance. For two different wavelengths of light (w' and w") passing through the same flow cell, the ratio of the absorbance of the substance at the two wavelengths is a constant:

$$Aw'/Aw'' = (a' \times b \times c)/(a'' \times b \times c) = \text{constant}.$$

This constant, $Aw'/Aw''$ is known as the absorbance ratio, and can be used to characterize pure chemicals in the same manner as density, boiling point, melting point, refractive index or chromatographic retention time.

However, if the measured absorbance at the two wavelengths, Aw' and Aw" represent retention times when more than one substance is present in the flow cell, the absorbance ratio is not a constant, but changes as the relative concentrations of the components within the flow cell change.

Absorbance ratio has formerly been measured by a sequential process of trapping the compound in the flow cell by stopping the flow, determining the absorbance at two wavelengths, and dividing the two absorbances to obtain the ratio. This method is slow, labor intensive and gives information at only one point.

Another known method for obtaining absorbance ratio is by using two separate detectors set at different wavelengths. The chromatograms obtained can be stored digitally in a computer and the two signals can then be divided to obtain the desired ratio. This method requires sophisticated data processing techniques, and cannot be done in real time because the two detector signals do not represent the same point in the chromatogram. Also, since the first flow cell will have a peak-spreading effect on the chromatogram, the second flow cell will not see the same concentration profile as the first and the peak ratio calculation will be in error.

A third method consists of running two chromatograms either simultaneously using two chromatographs or consecutively with a single device, with the detector(s) adjusted to detect at different wavelengths. The results are then compared either manually or by computer, resulting in the ratio, difference and/or sum. This method is time-consuming and inaccurate because the results depend on injecting exactly the same quantities of sample in the two runs. In practice, this is difficult to do with high accuracy without extraordinary precautions being taken.

SUMMARY OF THE INVENTION

The present invention provides a method and apparatus for detecting and analyzing the components of an eluent stream in a manner which makes it possible to effectively isolate pure components for accurate measurement or collection of such components, even if they are severely overlapped.

Generally described, the present invention provides a method and apparatus for continuously determining and indicating the purity of components of an eluent stream for differentiating and collecting only selected pure components of the stream, and for effectively removing from a chromatogram of overlapping components the signal attributable to one of the components, thus leaving a chromatogram of only the remaining component. The eluent stream is passed from a chromatograph column through a flow cell, a beam of light is also passed through the flow cell, the beam of light is split when it emerges from the flow cell into a first beam and a second beam of differing wavelengths, the intensities of the first and second beams are detected, and the detected intensities are converted into a first signal proportional to the absorbance of the light beam at the wavelength of the first beam and a second signal proportional to the absorbance of the beam of light at the wavelength of the second beam.

In order to continuously determine whether or not the substance passing through the flow cell is pure, the ratio of the first and second signals is continuously determined. If the ratio remains at a constant value as the eluent stream passes through the flow cell, this indicates that a single, pure component is passing through the flow cell. If, on the other hand, the ratio varies, this indicates that more than one component, such as a desired substance and an impurity, are present. The ratio can be continuously displayed in any known manner. If a multiple-pen chart recorder is utilized, the chromatogram and the ratio can be simultaneously displayed for comparison purposes.

In order to differentiate and collect a pure component, control circuitry is provided responsive to the absorbance ratio being constant to divert the eluent stream to a collection vessel, so that only a desired pure substance of the various substances in the eluent stream is collected.

In order to remove a selected component from a chromatogram to allow accurate measurement of a remaining component, the first and second light beams are converted into first and second signals proportional to the absorbance of the beams at their respective wavelengths, the magnitude of one of the signals is adjusted by a scaling factor equal to the absorbance ratio of the selected component at the wavelengths of the first and second beams, the adjusted and unadjusted signals are subtracted from one another, and the difference between the adjusted and unadjusted signals is displayed. Thus, the invention can completely remove one component of two overlapping components of a chromatogram, by scaling the absorbance signal for one of the components at one wavelength to equal that component's absorbance at the other wavelength. Upon subtraction of the signals, that component disappears, leaving the precise chromatogram that would be produced by a sample including only the pure remaining component. Highly accurate measurement of the retention time of the remaining component is thereby made possible.

Thus, it is an object of the present invention to provide a method and apparatus for effectively isolating overlapping components of a chromatogram without increasing the separation of the components by the chromatograph column.

It is a further object of the present invention to provide a method and apparatus for continuously determining the purity of components of a chromatogram.

It is a further object of the present invention to provide a novel method and apparatus for continuously determining the absorbance ratio of a component of a chromatogram.

It is a further object of the present invention to provide a method and apparatus for differentiating between pure components of an eluent stream and collecting selected pure components thereof.

It is a further object of the present invention to provide a method and apparatus for removing the signal attributable to a selected component of overlapping components of an eluent stream from a chromatogram derived from the eluent stream to produce a chromatogram of only the remaining pure component.

Other objects, features and advantages of the present invention will become apparent upon reading the following specification, when taken in light of the drawing and the appended claims.

BRIEF DESCRIPTION OF THE DRAWING

FIGS. 3(a)-(c) are schematic representations of chromatograms illustrating the use of an apparatus and method embodying the present invention to determine the purity of totally convoluted components of a chromatogram.

FIGS. 4(a)-(c) are schematic representations of chromatograms illustrating the use of an apparatus and method embodying the present invention to determine the purity of overlapping components of a chromatogram.

DETAILED DESCRIPTION

Figure 1:
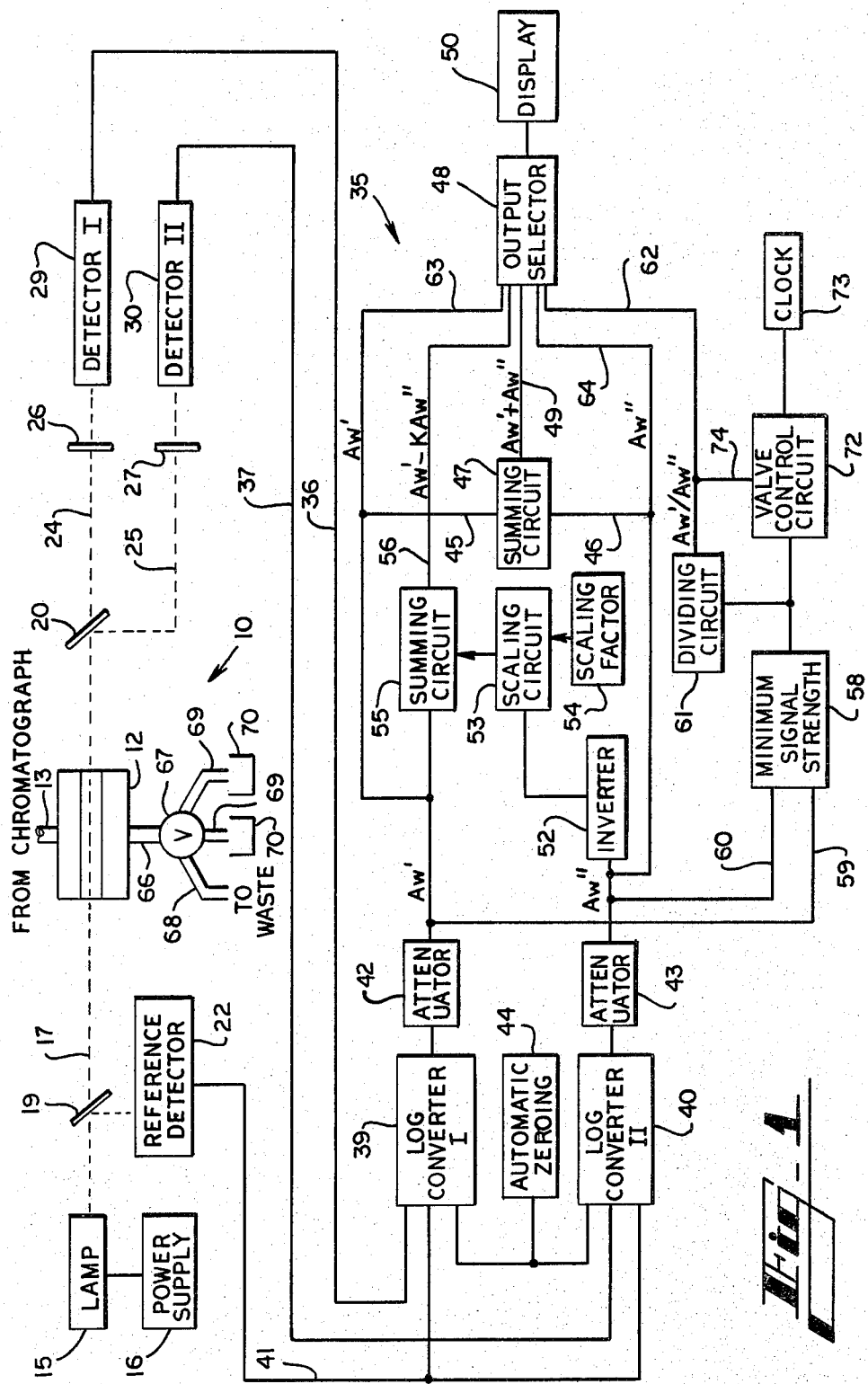
FIG. 1 is a schematic diagram of an apparatus embodying the present invention.

Referring now in more detail to the drawing, FIG. 1 is a schematic diagram of a detection system 10 embodying the present invention. A stream of eluent containing a sample that has been passed through a chromatograph column is passed through a flow cell 12 of conventional construction. Associated with the flow cell is a lamp 15, such as a deterium lamp, which provides a source of ultraviolet light. The lamp is energized by a power supply 16. A beam of light 17, shown as a dashed line in FIG. 1, is directed from the lamp 15 through the flow cell 12. However, located between the lamp 15 and the flow cell 12 is a beam splitter 19 which directs a known portion of the light beam 17 to a reference detector 22. The reference detector 22 is a photosensitive detector which converts the intensity of the light from the lamp 15 into an electrical signal which can be used to determine the intensity of the beam 17 before it passes through the flow cell 12.

After passing through the flow cell 12, the remainder of the light beam 17 is again split by a beam splitter 20, into a first beam 24 and a second beam 25. The first beam 24 passes through a first narrow band pass filter 26 which is selected to pass only a particular wavelength w'. A first photosensitive detector 29 receives the light of wavelength w' and converts its intensity into an electrical signal. The second beam 25 is passed through a second narrow band pass filter 27 which allows only a second particular wavelength w" to pass therethrough. The light of wavelength w" is detected by a photosensitive detector 30 of similar conventional construction to the detector 29.

As an alternative to the beam splitter 20, the beam emerging from the flow cell 12 can be directed onto a diffraction grating to divide the beam into its spectral components. The detectors 29 and 30 would then be placed in selected positions to intercept light of particular wavelengths reflected from the grating.

The electrical signals generated by detectors 29 and 30 corresponding to the intensities of the first and second beams 24 and 25, are directed along lines 36 and 37, respectively, to an analyzer circuit 35. It is known that the change in intensity of the light passing through the flow cell and detected by the detectors is proportional to the logarithm of the concentration of sample components in the eluent stream passing through the flow cell 12. In order to obtain an electrical signal proportional to the absorbance of the components passing through the flow cell 12, the signals from the detectors 29 and 30 are connected to conventional first and second log converters 39 and 40, respectively. The output of the reference detector 22 is also input to the log converters 39 and 40 so that the change in intensity of the light beams can be determined. The first log converter 39 outputs a first signal proportional to the absorbance of light of wavelength w' by the components in the flow cell 12. This electrical signal is adjusted in a conventional manner by an attenuator 42 which outputs the adjusted absorbance signal Aw'. Line 37 from the second detector 30 is connected to a second log converter 40 and attenuator 43, resulting in a second output signal Aw''. An automatic zeroing circuit 44 of known construction is connected to both the log converters 39 and 40. The manually operated automatic zeroing circuit 44 simultaneously adjusts the zero offset of both the first and second signals to assure that when no component is present in the flow cell 12, both the first and second signals are at zero voltage. This is necessary for accurate analysis by the analyzer circuit 35.

The analyzer circuit 35 is capable of performing several analyses of the first and second signals Aw' and Aw'', and displaying the results of these analyses. The signals Aw' and Aw'' output from the attenuators 42 and 43, respectively, are connected along lines 45 and 46, respectively, to a summing circuit 47. The summing circuit 47 is also of conventional construction and outputs a signal Aw'+Aw'' to an output selector 48 which is connected to a display apparatus 50. The display apparatus 50 may be, for example, a numerical readout or a multiple channel chart recorder. If the display apparatus 50 is, for example, a dual pen chart recorder, then the output selector 48 is a circuit which permits manual selection of which signals from the analyzer 35 will be displayed by the pens of the chart recorder.

The first and second signals Aw' and Aw'' are also provided along lines 59 and 60, respectively, to a conventional minimum signal strength analyzer 58. The output of the minimal signal strength detector 58 is provided to a conventional dividing circuit 61, the output of which is the ratio of the first and second signals, Aw'/Aw''. The minimum signal strength detector 58 provides its output to the dividing circuit 61 only when the signals Aw' and Aw'' are above a minimum threshold value. This prevents the dividing circuit 61 from attempting to divide by a value that is very near to zero when no component is eluting through the flow cell 12. Thus, an undesirable operation resulting in an infinitely high output is avoided. The ratio signal from the dividing circuit 61 is connected to the output selector 48 along line 62.

The second signal Aw'' is also provided to an inverter 52 which converts the signal Aw'' to $-$Aw''. The output of the inverter 52 is connected to a scaling circuit 53 which is also connected to a scaling factor input circuit 54. The scaling factor input circuit 54 provides for the manual input of a scaling factor k, such as the absorbance ratio of a selected substance at the wavelengths w' and w'', to the scaling circuit 53. The scaling factor is stored by the circuit 54 for use throughout the chromatograph run. When the absorbance ratio is used, it can be obtained either from a previous run of the same substance, in which case the absorbance ratio is the output of the dividing circuit 61, or by using a textbook value or a value for the ratio obtained from prior experience of the operator. The scaling circuit 53 adjusts the magnitude of the inverted signal $-$Aw'' by continuously multiplying the inverted signal by the scaling factor input through the scaling factor input circuit 54. The adjusted signal output from the scaling circuit 53 is connected to a summing circuit 55, the other input of which is the first signal Aw'. The summing circuit 55 is of conventional construction, and adds its inputs to provide an output Aw'$-$kAw''.

If two substances, X and Y, are present simultaneously in the flow cell, then the measured absorbance at wavelength w' is:

$$Aw' = Xw' + Yw',$$

and the measured absorbance at wavelengths w'' is:

$$Aw'' = Xw'' + Yw''.$$

Since the absorbance ratio for X, Xw'/Xw'', is a constant, it will be seen that $$Xw' - kXw'' = 0.$$

Therefore, if the absorbance chromatogram Aw'' is multipled continuously by a scaling factor k equal to the absorbance ratio, when the retention time of the component X is reached, the absorbance component at wavelength w'', kXw'', will be identical to the absorbance component at wavelength w', Xw'. If the adjusted absorbance chromatogram kAw'' is then subtracted from the adjusted absorbance chromatogram Aw', the components kXw'' and Xw' will cancel one another. The resulting differential chromatogram will then show only $$Aw' - kAw'' = Yw' - kYw''$$

and this peak can be measured to obtain the precise retention time of component Y without interference from the overlapping component X.

Figure 2:
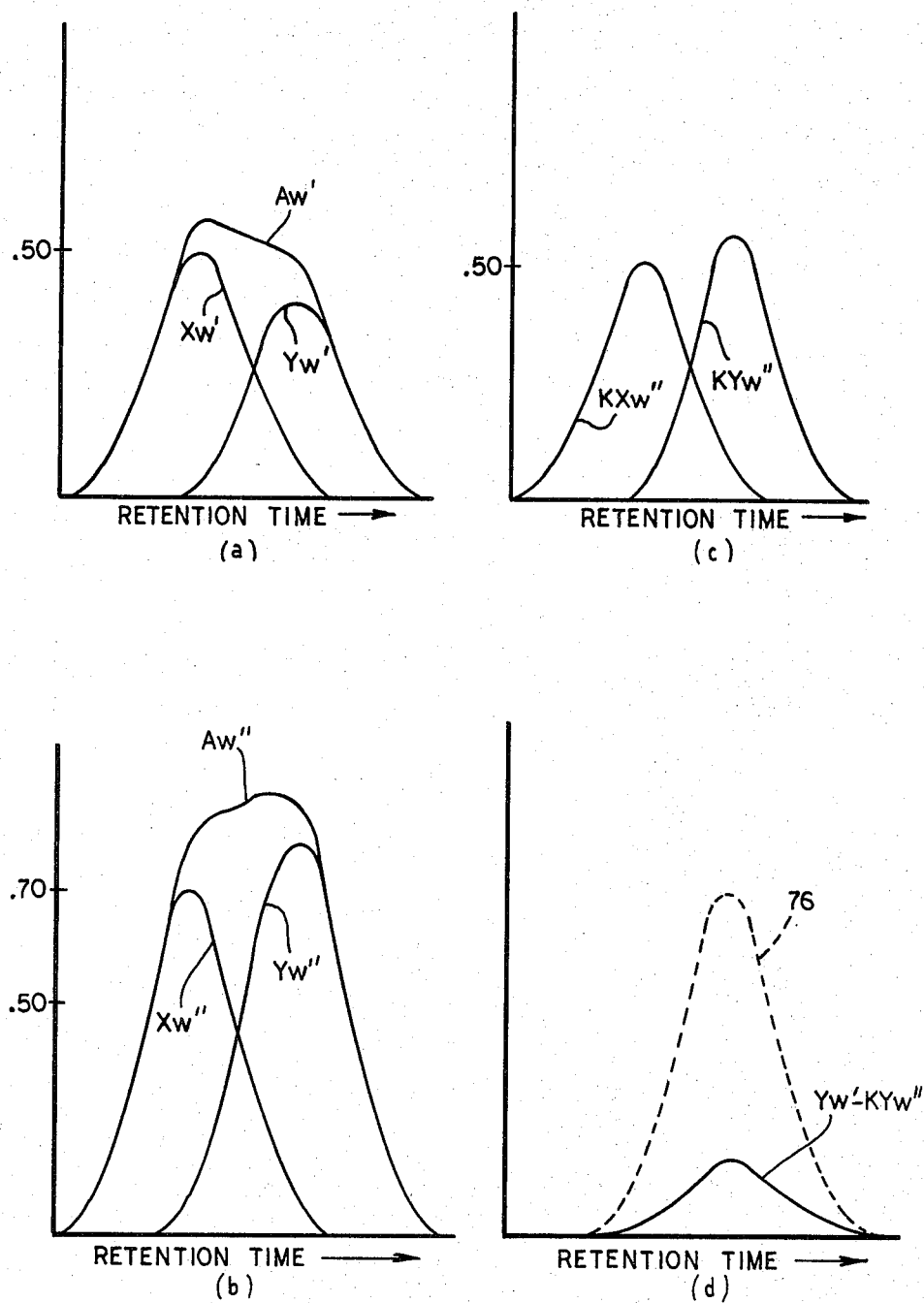
FIGS. 2(a)-(d) are schematic representations of chromatograms illustrating the removal of an overlapping component utilizing an apparatus embodying the present invention.

The elimination of the component X is shown diagrammatically in FIG. 2. FIG. 2(a) shows the chromatogram of a convoluted peak of the first signal Aw'. The convoluted peak Aw' is composed of two components X and Y, the pure form of each of the components also being shown in FIG. 2(a). FIG. 2(b) shows the chromatogram of the same peak at wavelength w''. The second signal Aw'', and the component peaks Xw'' and Yw'' are again shown. In FIG. 2(c) the results of operation of the scaling circuit 53 are diagrammatically shown. The component peaks Xw'' and Yw'' have been scaled down by multiplication by the absorbance ratio k for the component X at the two wavelengths w' and w'', where k=Xw'/Xw''. Therefore, the component peak Xw' in FIG. 2(a) is identical to the adjusted component peak kXw'' in FIG. 2(c). FIG. 2(d) shows the output of the summing circuit 55, which is:

Aw'$-$kAw''=Yw'$-$kYw''. The curve shown in FIG. 2(d) would be shown with a negative displacement on the chart recorder, although it is shown with a positive displacement in the figure. The differential signal can be amplified to provide for more accurate measurement of the location of the peak, as shown by the dotted curve 76 in FIG. 2(d). The differential signal from the summing circuit 55 is provided along a line 56 to the output selector 48 for selective display by the display apparatus 50.

In addition to the above-described signals resulting from analysis by the analyzer circuit 35, the first signal Aw' is connected along a line 63 directly to the output selector 48, and the second signal Aw'' is also directly provided to the output selector 48 along line 64.

The use of the absorbance ratio to determine the purity of components in convoluted or overlapping peaks of a chromatogram is shown in FIGS. 3 and 4. In FIG. 3, the first and second signals Aw' and Aw'' appear upon visual inspection to represent pure components eluting through the flow cell 12. However, when the absorbance ratio, that is, the output of the dividing circuit 61, is plotted simultaneously with the signals, the varying value of the absorbance ratio indicates that the eluting substance is impure. This plot is shown in FIG. 3(a). FIG. 3(b) and (c) show diagrammatically the pure peak components for wavelengths w" and w', respectively. It will be seen that pure elution of the components X and Y occurs outside the dashed lines 77, which coincides with the locations where the absorbance ratio curve is horizontal, or constant.

In FIG. 4, a similar analysis is shown for overlapping peaks that are not completely convoluted. Again, it will be seen that elution of pure components is obtained only at the horizontal portions of the ratio plot outside the dashed lines 77.

In accordance with the present invention, the absorbance ratio analysis of the analyzer circuit 35 can be used to accumulate pure samples of a desired substance or substances. In order to accomplish such collection, the eluting liquid flowing through the flow cell 12 is directed through a conduit 66 to a multi-position valve 67. As shown in FIG. 1, the valve has three positions, one opening to a line 68 to waste, and the other opening to lines 69 opening to a pair of collection receptacles 70. The valve 67 is controlled by a valve control circuit 72 which forms a part of the analyzer circuit 35. The valve control circuit 72 has as its inputs the absorbance ratio signal from the dividing circuit 61 along a line 74, the output of the minimum signal strength detector 58, and the output of a clock 73 representing the retention time from the beginning of the chromatograph run. The valve control circuit 72 contains logic circuitry the construction of which is within the skill of the art. If the minimum signal strength detector indicates that a peak is being detected, the circuit 72 then determines whether the absorbance ratio is equal to the known value for the substance desired to be collected. If so, the circuit 72 determines whether the slope of the absorbance ratio curve is zero, in which case the absorbance ratio is constant. If so, the circuit 72 determines whether the retention time input by the clock 73 is the known retention time for the desired substance. If this is also true, then the valve control circuit 72 causes the valve 67 to switch from its waste position to the position for directing the eluent stream into one of the receptacles 70 for collection of the desired substance. As soon as the absorbance ratio begins to vary, the valve position is changed back to waste. When the next desired component begins to elute, and the retention time and absorbance ratio values are correct for that substance, the valve control circuit 72 will change the position of the valve 67 to another output line 69 for collection of the second substance so long as the absorbance ratio remains constant.

It will be seen from the foregoing that the present invention greatly improves the capability of one in the chromatography art to differentiate and measure pure components of an eluent stream without resorting to complex and expensive methods of improving the separating efficiency of the chromatograph column.

While this invention has been described in detail with particular reference to preferred embodiments thereof, it will be understood that variations and modifications can be effected within the spirit and scope of the invention as described hereinbefore and as defined in the appended claims.

We claim:

1. In a liquid chromatograph, a detection system comprising:
   a flow cell for receiving a continuous flow of eluent including a plurality of components separated according to retention time by said chromatograph;
   means for passing a beam of light through said flow cell;
   means subsequent to said flow cell for splitting said beam of light into two beams of selected differing wavelengths;
   detector means for detecting each of said beams;
   means responsive to each of said detector means for converting said beams into a first electrical signal proportional to the absorbance of one of said beams by the component passing through said flow cell at said selected wavelength of said one of said beams, and a second electrical signal proportional to the absorbance of said component at said selected wavelength of said other of said beams;
   ratio means for continuously determining the ratio of said first and second signals and providing a ratio signal;
   and means for simultaneously displaying said first signal, said second signal and said ratio signal.

2. The apparatus of claim 1, further comprising means, operative independently of said ratio means, for continuously adjusting the magnitude of said first signal to provide an adjusted first signal by a scaling factor selected to equalize said first signal and said second signal at the time of detection of a preselected component of said eluent; means for continuously finding the difference between said adjusted first signal and said second signal; and means for continuously displaying said difference between said second signal and said adjusted first signal.

3. The apparatus of claim 1 further comprising a means for collecting a selected pure component of said eluent, including valve means, responsive to said retention time corresponding to said selected component and said ratio being a constant valve corresponding to said selected component, for diverting said eluent into a receptacle.

4. The apparatus of claim 1, wherein said ratio means for determining the ratio of said signals is operative only when the magnitude of each of said first and second signals is above a predetermined minimum value.

5. In a liquid chromatograph, a detection system comprising:
   a flow cell for receiving a continuous flow of eluent including a plurality of components separated according to retention time by said chromatograph;
   means for passing a beam of light through said flow cell;
   means for splitting said beam of light into two beams of selected differing wavelengths;
   detector means for detecting each of said beams;
   circuit means responsive to each of said detector means for converting said beams into a first electrical signal proportional to the absorbance of one of said beams by the eluent passing through said flow cell at said selected wavelength of said one of said beams, and a second electrical signal proportional to the absorbance of the other of said beams by said eluent at said selected wavelength of said other of said beams;
   means for continuously determining the ratio of said first and second signals; and means for collecting a selected pure component of said eluent, including valve means, responsive to said retention time corresponding to said selected component and said ratio being a constant value corresponding to said selected component, for diverting said eluent into a receptacle.

6. In a method of generating a liquid chromatogram including passing an eluent having a plurality of components therein through a chromatograph column to separate said components according to retention time, subsequently passing said eluent through a flow cell while passing a beam of light through said flow cell, and detecting the intensity of said beam of light after passing through said flow cell, the improvement comprising the steps of:
  splitting said beam emerging from said flow cell into a first beam and a second beam of differing wavelengths;
  detecting the intensity of said first and second beams;
  converting said detected intensities into a first signal proportional to the absorbance by said eluent at the wavelength of said first beam and a second signal proportional to the absorbance by said eluent at the wavelength of said second beam;
  continuously determing the ratio of said first and second signals and providing a ratio signal; and
  simultaneously displaying said first signal, said second signal and said ratio signal.

7. In a method of generating a liquid chromatogram including passing an eluent having a plurality of components therein through a chromatograph column to separate said components according to retention time, subsequently passing said element through a flow cell while passing a beam of light through said flow cell, and detecting the intensity of said beam of light after passing through said flow cell, the improvement of collecting a pure component, comprising the steps of:
  splitting said beam emerging from said flow cell into a first beam and a second beam of differing wavelengths;
  detecting the intensity of said first and second beams;
  converting said detected intensities into a first signal proportional to the absorbance by said component at the wavelength of said first beam and a second signal proportional to the absorbance by said component at the wavelength of said second beam;
  continuously determining the ratio of said first and second signals; and
  responsive to said ratio remaining constant at a predetermined retention time, collecting said eluent.

* * * * *